United States Patent [19]

Lech et al.

[11] Patent Number: 5,641,536
[45] Date of Patent: Jun. 24, 1997

[54] TABLET COATING METHOD

[75] Inventors: Stanley Lech, Rockaway; John Denick, Jr., Newton, both of N.J.

[73] Assignee: Warner-Lambert Company, Morris Plains, N.J.

[21] Appl. No.: 470,813

[22] Filed: Jun. 6, 1995

Related U.S. Application Data

[62] Division of Ser. No. 113,476, Aug. 30, 1993, abandoned.

[51] Int. Cl.$^6$ .............................. A61J 3/06; B05D 3/04; B05D 3/12; A61K 9/30
[52] U.S. Cl. .................... 427/2.14; 427/2.22; 427/212
[58] Field of Search .............................. 427/2.14, 2.18, 427/2.19, 2.22, 212, 378

[56] References Cited

U.S. PATENT DOCUMENTS

| | | | |
|---|---|---|---|
| 3,935,326 | 1/1976 | Groppenbacher | 427/3 |
| 4,302,440 | 11/1981 | John | 424/35 |
| 4,511,553 | 4/1985 | Boesig | 424/35 |
| 4,556,552 | 12/1985 | Porter | 424/32 |
| 4,572,833 | 2/1986 | Pedersen | 424/20 |
| 4,606,909 | 8/1986 | Bechgaard | 424/21 |
| 4,704,295 | 11/1987 | Porter | 427/3 |
| 4,800,087 | 1/1989 | Mehta | 424/497 |
| 4,802,924 | 2/1989 | Woznicki et al. | 427/2.18 |
| 4,816,264 | 3/1989 | Phillips | 424/472 |
| 4,855,326 | 8/1989 | Fuisz | 514/772 |
| 4,873,085 | 10/1989 | Fuisz | 514/772 |
| 4,970,081 | 11/1990 | Frisbee | 424/480 |
| 4,997,856 | 3/1991 | Fuisz | 514/777 |
| 5,011,532 | 4/1991 | Fuisz | 106/215 |
| 5,028,632 | 7/1991 | Fuisz | 514/772 |
| 5,034,421 | 7/1991 | Fuisz | 514/772 |
| 5,047,258 | 9/1991 | Belanger | 427/2.19 |
| 5,096,492 | 3/1992 | Fuisz | 106/215 |
| 5,098,715 | 3/1992 | McCabe | 424/479 |
| 5,248,516 | 9/1993 | Wheatley et al. | 427/2.14 |
| 5,370,881 | 12/1994 | Fuisz | 426/5 |
| 5,387,431 | 2/1995 | Fuisz | 426/658 |

FOREIGN PATENT DOCUMENTS

| | | |
|---|---|---|
| 0551700 | 7/1993 | European Pat. Off. . |
| 2605334 | 8/1977 | Germany . |
| 1178622 | 8/1966 | United Kingdom . |
| 8707902 | 12/1987 | WIPO . |
| 8808298 | 11/1988 | WIPO . |
| 9311750 | 6/1993 | WIPO . |

*Primary Examiner*—Diana Dudash
*Attorney, Agent, or Firm*—Michael J. Atkins

[57] ABSTRACT

A method for coating pharmaceutical tablets is disclosed in which polymeric coating ingredients are combined with saccharides in a melt spinning operation to form composite particulates. The particulates are then dispersed in water to form an aqueous polymer coating solution, followed by application to pharmaceutical tablets by such methods as spray coating. The particulates dissolve extremely rapidly in water to form a dispersion of the polymer coating ingredients. Such rapid dissolution allows for increased processing rates and avoids disadvantages of the prior art such as the requirement of high shear rate mixing for long times.

17 Claims, No Drawings

TABLET COATING METHOD

This is a divisional of the U.S. application Ser. No. 08/113,476, filed Aug. 30, 1993, now abandoned.

BACKGROUND OF THE INVENTION

1. Field of the Invention

The present invention relates to coated pharmaceutical dosage units such as tablets and the like. In particular, the invention relates to an improved method for coating pharmaceutical tablets with an aqueous polymer solution.

2. Brief Description of the Prior Art

Numerous methods for coating pharmaceutical tablets are known. They include sugar coating, solvent film coating, aqueous film coating, delayed release coating and granule coating techniques.

Pharmaceutical tablets have been coated for a variety of reasons, including masking objectionable flavors or odors, protecting unstable tablet compositions, improving the ease with which the tablets are swallowed, providing protection of the tablets through the stomach with enteric coatings and improving the appearance of the tablets. For example, aspirin tablets and other tablets that are powdery and friable have been treated with a variety of coatings to keep them from dissolving too soon.

In the past, sugar coating was the most commonly used coating technique. However, disadvantages of sugar coating such as relatively high cost, long coating time and high bulk have led to the use of other coating materials. Some of the most commonly used coatings today are polymeric film coating agents. Advantages of polymeric coatings include the ability to produce a tablet having a coating that comprises less than 3% of its weight, better resistance to chipping and increased tablet strength. Polymers have been applied to pharmaceutical tablets using both aqueous and non-aqueous solvents.

Various methods for coating tablets with polymeric solutions are known, including rotating pan, fluid bed, spouted bed, coascervation tank and pressing methods. In most coating methods, the coating solutions are sprayed onto the tablets as the tablets are being agitated in a pan, fluid bed, etc. As the solution is being sprayed, a thin film is formed that adheres directly to each tablet. The coating may be formed by a single application or may be built up in layers through the use of multiple spraying cycles.

Rotating coating pans are often used in the pharmaceutical industry. Uncoated tablets are placed in the pan, which is typically tilted at an angle from the horizontal, and the liquid coating solution is introduced into the pan while the tablets are tumbling. The liquid portion of the coating solution is then evaporated by passing air over the surface of the tumbling tablets. In contrast, a fluid bed coater operates by passing air through a bed of tablets at a velocity sufficient to support and separate the tablets as individual units. Once separated, the tablets are sprayed with the coating composition.

Typical spray coating solutions include polymers, plasticizers, dyes and other ingredients dissolved or dispersed in an aqueous or non-aqueous medium. Aqueous systems are preferred due to lower costs and environmental compatability. However, a major disadvantage of conventional aqueous polymer coating methods is that they require relatively long mixing times at high shear rates in order to disperse the polymeric ingredients in water. Such long mixing times are detrimental because they result in significant reductions in processing rates. Furthermore, the high shear rates required for mixing the polymers, and the long times required for such mixing, cause excessive foaming of the solutions, resulting in further time delays while the foam dissipates. Antifoaming agents can be used to reduce foaming problems, but they increase costs.

U.S. Pat. No. 4,302,440 issued Nov. 24, 1981 to John et al. discloses a method for aqueous spray coating hydroxypropyl methylcellulose onto the exterior surface of aspirin tablets. The aqueous solution comprises 2–15 weight % hydroxypropyl methylcellulose and 15–25 weight % plasticizer based on the hydroxypropyl methylcellulose. The solution is sprayed onto uncoated aspirin tablets as they rotate in a baffled pan. This patent and all other patents cited herein are hereby incorporated by reference.

U.S. Pat. No. 4,970,081 issued Nov. 13, 1990 to Frisbee discloses aqueous coating solutions containing an acrylate/methacrylate copolymer, hydroxypropyl methylcellulose, sodium chloride and talc. The solution is coated on aspirin granules to provide controlled release.

U.S. Pat. No. 4,816,264 issued Mar. 28, 1989 to Phillips et al. discloses aqueous coating solutions containing multiple polymers such as hydroxypropyl cellulose and acrylic resin. The solution may also contain other ingredients such as antifoam agents, plasticizers and flavoring agents. The coating solution is used in a rotating pan to coat several different types of drug tablets.

U.S. Pat. No. 5,047,258 issued Sep. 10, 1991 to Belanger et al. discloses a process for spray coating tablets that utilizes an acrylate enteric polymer and plasticizer in water. The spray coating solution requires no anti-adherent such as talc. The spray coating operation is carried out with conventional rotating perforated pans.

U.S. Pat. No. 5,098,715 issued Mar. 24, 1992 to McCabe et al. discloses a method for aqueous spray coating tablets using solutions containing polymer, plasticizer, flavoring and sweetening ingredients. Titanium dioxide or other opacifying agents or colorants may optionally be used in the coating solutions.

U.S. Pat. No. 3,935,326 issued Jan. 27, 1976 to Groppenbacher et al. discloses a process for coating tablets using a synthetic resin dispersed in water.

U.S. Pat. No. 4,572,833 issued Feb. 25, 1986 to Pedersen et al. discloses a method for coating pharmaceutical tablets using organic or aqueous solutions. When an aqueous solution is used, the solution includes a hydrophobic substance such as wax and is applied at a temperature above the melting temperature of the hydrophobic material. A fluidized bed or rotating pan may be used to coat the tablets.

U.S. Pat. No. 4,606,909 issued Aug. 19, 1986 to Bechgaard et al. discloses the use of organic solvents or aqueous solutions for coating pharmaceutical units. The aqueous solutions include acrylic polymers and produce coatings that are insoluble below a pH of 7.

U.S. Pat. No. 4,800,087 issued Jan. 24, 1989 to Mehta discloses a method for microencapsulating pharmaceutical cores using an aqueous polymer coating. In addition to polymers, the coating solution may contain diluents, fillers, bulking agents, plasticizers, pigments and opacifiers.

U.S. Pat. No. 4,556,552 issued Dec. 3, 1985 to Porter et al. discloses a method of spray coating pharmaceutical tablets using a dry powder that is mixed with water to form a coating suspension. The powder comprises polymer, plasticizer, pigment and anticaking ingredients. After the powder is mixed with water, an ammonia solution is added to the suspension, followed by spraying of the suspension onto the pharmaceutical tablets.

U.S. Pat. No. 4,511,553 issued Apr. 16, 1985 to Boesig et al. discloses a coating process using an aqueous solution of saccharose and at least one additional sugar such as lactose. Additional flavors, fragrances, and coloring ingredients may be added to the aqueous solution. The solution may be used to coat pharmaceutical tablets, chocolate centers and hazel nuts.

U.S. Pat. No. 4,704,295 issued Nov. 3, 1987 to Porter et al. discloses a method for coating pharmaceutical tablets utilizing a dry powder that is added to water and then sprayed onto the tablets.

U.S. Pat. Nos. 4,855,326, 4,873,085, 4,997,856, 5,011,532, 5,028,632, 5,034,421 and 5,096,492 issued to Fuisz disclose methods of producing filaments comprising various ingredients combined with a sugar carrier. The filaments are produced by a spinning technique similar to that used for making cotton candy. The ingredients, such as medicaments or cosmetics, are combined with the sugar carrier, and the mixture is then spun to form high aspect ratio fibers.

The present invention has been developed in view of the foregoing and to overcome the deficiencies of the prior art.

SUMMARY OF THE INVENTION

An object of the present invention is to provide a novel method for coating pharmaceutical tablets.

Another object of the present invention is to provide a method for coating pharmaceutical tablets comprising the steps of melt spinning a mixture of saccharide and polymer coating ingredients to form particulates, mixing the particulates with water to form a coating solution, spray coating pharmaceutical tablets with the solution and drying the coated tablets.

A further object of the present invention is to provide a coated pharmaceutical tablet made by the method of melt spinning a mixture of saccharide and polymer coating ingredients to form particulates, mixing the particulates with water to form a coating solution, applying the aqueous solution to pharmaceutical tablets and drying the coated tablets.

Another object of the present invention is to provide composite particulates for use in coating pharmaceutical tablets. The particulates comprise saccharide and polymer coating ingredients, and are capable of dissolving extremely rapidly in water.

As used herein, the term "saccharide" is broadly defined to include monosaccharides, disaccharides, polysaccharides and sugars.

These and other objects of the invention will become more readily apparent from the following description.

DETAILED DESCRIPTION OF THE PREFERRED EMBODIMENTS

The present invention relates to a method for coating pharmaceutical tablets in which a melt spinning technique is used to form particulates comprising saccharide and polymer coating ingredients. These particulates are then mixed with water to form a coating solution or suspension. The coating solution is applied to pharmaceutical tablets and the solution is dried to form a solid polymeric coating.

In the melt spinning step, at least one saccharide selected from monosaccharides, disaccharides, polysaccharides and sugars is combined with polymer coating ingredients to form a mixture that is then subjected to the melt spinning process. The process yields composite particulates comprising a combination of the saccharide and polymer coating ingredients. These particulates are then added to water to form a coating solution in which the polymer coating ingredients are substantially uniformly dispersed. In accordance with the present invention, the use of saccharide-containing composite particulates has been found to significantly accelerate the dispersion of the polymer coating ingredients in water. The use of high shear rate mixing for long periods of time is therefore avoided. Once the polymer coating ingredients are dispersed in water, the resulting solution is used to coat pharmaceutical tablets by methods such as spray coating.

The particulates typically comprise from about 20 to about 99 weight % saccharide and from about 1 to about 80 weight % polymer coating ingredients. Preferably, the saccharide comprises from about 40 to about 90 weight % of the particulates, and more preferably from about 60 to about 80 weight %.

Suitable saccharides include sucrose, lactose, maltose, polydextrose, dextrans, corn syrup, corn syrup solids, sorbitol, xylitol and combinations thereof. Preferred saccharides include sugars such as sucrose, lactose and maltose, and polydextrose and dextrans. Alcohol sugars are particularly preferred. Since the saccharides are melted during the melt spinning process, they should have a melting point that is below the temperature at which adverse reactions of the polymer coating ingredients occur.

The polymer coating ingredients comprise at least one coating polymer and may include plasticizers, colorants, opacifiers, glidants, flavoring agents, diluents, fillers, bulking agents and other ingredients suitable for use in polymeric coatings. Suitable polymers include cellulose ethers, vinyls, glycols and acrylics. Of the cellulose ethers, hydroxypropyl methylcellulose, hydroxypropyl cellulose, methylcellulose and ethylcellulose are suitable. Polyvinylpyrrolidone, polyethylene glycols, methacrylic amino ester copolymers, sodium alginate, povidone and gelatin are also suitable coating polymers. A particularly preferred coating polymer is hydroxypropyl methylcellulose (HPMC). Many other polymers are suitable for use in accordance with the present invention, as long as they possess satisfactory solubility, permeability and mechanical characteristics in the final coating form. The polymers must be sufficiently soluble in the gastrointestinal tract, must be sufficiently impermeable to moisture and must possess satisfactory tensile strength, elastic modulus and film adhesion characteristics. In general, polymers having increased molecular weight tend to possess increased tensile strength and elastic modulus but decreased film adhesion characteristics. Multiple polymers may be combined to form the coating polymer.

The polymer coating ingredients of the present invention preferably include a plasticizer. The use of a plasticizer promotes softening and ease of deformation of the polymer, and may also reduce the glass transition temperature of the polymer. External plasticizers are preferred and typically comprise a low molecular weight liquid. Such plasticizers typically comprise from about 1 to about 40 weight % of the polymer coating ingredients based on the weight of the polymer. Typical plasticizers include glycerin, propylene glycol, low molecular weight polyethylene glycols, triacetin, sorbitol, acetylated monoglycerides, citrate esters, phthalate esters, mineral oil and vegetable oils. A preferred plasticizer is polyethylene glycol MW 4000.

Colorants, opacifiers and glidants may also be included with the polymer coating ingredients in order to improve the appearance and other characteristics of the coating. Suitable colorants and opacifiers include water soluble dyes, water insoluble pigments and natural colorants. Examples of suitable colorants include D&C and FD&C Blue, Red and Yellow lakes and dyes. A preferred natural colorant is carmel. The amount of colorant used depends upon the appearance desired and can be adjusted accordingly. Pigments including titanium dioxide, calcium carbonate, calcium sulfate, magnesium oxide, magnesium carbonate, aluminum silicate, aluminum hydroxide, talc and iron oxide may be used due to their uniformity, stability and hiding power. Metal oxides are preferred opacifiers, with titanium dioxide being a particularly preferred opacifier. Opacifiers can be advantageously used to increase hiding power while reducing the amount of colorant necessary. Thus, the use of a relatively inexpensive, inorganic opacifier such as titanium dioxide can minimize the use of relatively expensive colorants. Examples of glidants for improved processing and to reduce coating tackiness are talc, metal stearates, inorganic clays, silicas, natural and synthetic waxes and oils.

In accordance with the present invention, the polymer coating ingredients are combined with the saccharide to form a mixture that is subjected to a melt spinning process. In the melt spinning process, the mixture is heated, typically above the melting point of the saccharide, in a spinning head having appartures in the sides thereof. Once the mixture is heated to the appropriate temperature, the head is rotated and the mixture is ejected from the appartures by centrifugal force. A suitable spinning machine is the Econofloss Model 3017 manufactured by Gold Medal Products Company. The rotation speed and temperature of the mixture during spinning may be adjusted to achieve the desired particulate morphology. Rotation speeds of from 3000 to 5000 rpm are preferred, with 4000 rpm being a particularly preferred speed. The aperature size or slit width of the spinning head can be adjusted to produce the desired size of particulates.

In accordance with the present invention, the spun material is in the form of composite particulates which comprise a combination of the polymer coating ingredients and saccharide. The particulates preferably have an average size of from about 0.1 to about 8 mm. The particulates are advantageously formed in the shape of equiaxed particles, flakes, rods and the like, having relatively low aspect ratios. It is preferred that the particulates possess an average aspect ratio of less than 20:1 and more preferably less than 10:1. Such a low aspect ratio morphology results in durable particulates having minimal friability. The low aspect ratio particulates are easily handled in the subsequent coating process, substantially reducing dust problems associated with conventional polymer coating powders.

The composite particulates of the present invention, comprising polymer coating ingredients in combination with saccharides, have been found to significantly improve the dispersion of the polymer coating ingredients once the particulates are added to water. In conventional aqueous spray coating processes, the coating ingredients such as polymers, plasticizers and colorants are added to water in loose powder form. These powders do not readily mix with water. Instead, the powders are non-wetted and tend to agglomerate. As a result, high shear rate mixing for long periods of time is required for preparing conventional aqueous polymer coating solutions. In addition to non-wetting and aglomeration problems, conventional polymer coating powders suffer from handling problems. Large amounts of dust are often produced during the preparation of conventional aqueous coating solutions because the coating ingredients are provided in loose powder form that readily becomes airborne. The particulates of the present invention substantially eliminate such problems because the polymer coating ingredients are combined together with saccharide in a particulate form that avoids the use of fine powders and promotes dispersion of the coating ingredients in water. When the particulates of the present invention are added to water, they typically dissolve within a few seconds with only minimal stirring. In contrast, prior art polymeric powders can take hours or even days to dissolve. Even with the use of high shear rate mixing techniques, conventional polymeric powders require excessively long times for satisfactory dispersion. Such high sheer rate mixing techniques are costly due to the relatively complex machinery involved and the requirement of additional ingredients such as antifoaming agents. The particulates of the present invention produce surprisingly superior results in comparison to prior art powder coating ingredients as illustrated in the following Example 1. The examples provided herein are for illustrative purposes only and are not intended to limit the scope of the present invention.

EXAMPLE 1

A polymer coating composition is prepared by mixing 88 weight % hydroxypropyl methylcellulose (HPMC) polymer, 2 weight % total titanium dioxide opacifier and FD&C blue colorant, and 10 weight % polyethylene glycol plasticizer. The mixture is divided in half and one sample weighing 57 grams is mixed with 170 grams of saccharide in the form of corn syrup solids. This mixture is subjected to a melt spinning process using an Econofloss model 3017 at a temperature of 150° C. and a head rotation speed of about 4000 rpm to form particulates comprising about 25 weight % polymer coating ingredients in combination with about 75 weight % saccharide. The particulate sample and the powder sample are each added to 148 milliliters of water at room temperature with gentle stirring. The particulate sample completely dissolves within 3 minutes, forming a uniform dispersion. The powder sample agglomerates upon addition to the water and does not disperse after 3 hours of stirring.

The particulates of the present invention may be added to water in amounts of from about 5 to about 80 weight % and preferably from about 30 to about 60 weight %. When mixed, the saccharide readily dissolves in the water and the polymeric coating ingredients are also dissolved or dispersed in the water to form an aqueous coating solution. Dissolution typically takes less than about 3 minutes and usually less than about 20 seconds. The term "solution" is defined broadly in accordance with the present invention to include true solutions of the polymeric coating ingredients in water and also dispersions of the polymer coating ingredients in water. Once dissolved, the aqueous coating solutions preferably contain concentrations of the coating polymer of from about 1 to about 30%, and more preferably from about 3 to about 15%.

When the particulates are added to water, it is preferred to use low sheer rate mixing. "Low sheer rate mixing" is defined in accordance with the present invention as that amount of mixing or agitation in which substantially no vortex or aeration of the solution occurs.

Once the aqueous coating solution is formed by the method of the present invention, the solution is applied to pharmaceutical tablets in any suitable manner. It is preferred to spray coat the pharmaceutical tablets using a rotating pan or other device. However, other coating methods may also be satisfactory. The term "pharmaceutical tablet" is defined broadly in accordance with the present invention to include a wide variety of pharmaceutical units such as tablets, capsules, granules, crystals and powders. While the coating of pharmaceutical tablets is the primary object of the present invention, it is also recognized that other tablets may be coated by the present methods. For example, other edible items such as confections can be coated by the methods of the present invention.

As stated above, the coating solutions prepared in accordance with the present invention can be applied to pharmaceutical tablets by various coating techniques, with the use of spray coating being the most preferred. In the spray coating process, the pharmaceutical tablets are placed in a rotating pan or other suitable vessel and the coating solution is sprayed onto the tablets as the tablets are agitated. Vessels such as rotating pans are commercially available for tablet coating purposes. The equipment necessary for spraying the coating solution includes a pumping system and at least one spray gun, which are also commercially available. Both air spray and airless spray coating techniques are suitable. Spraying parameters such as flow rate and spray time are controlled in a manner known in the art in order to produce the desired coating. The spraying operation can be carried out in a single step or in multiple steps in which layers of coating material are built-up on the tablets.

During the coating process, the coatings are dried in order to remove the water and to obtain a solid coating. It is particularly preferred to use forced air convection drying wherein the inlet air temperature, inlet air humidity and exhaust air volume are controlled in order to optimize drying rates. In the preferred rotating pan spray coating method, spraying and drying typically occur simultaneously during the coating process. It is thus necessary to adjust the drying parameters to take into account such factors as the surface area of the tablets, pan dimensions, degree of atomization of the spray, spray gun placement, pan speed and spray rate. Such parameters can be adjusted to achieve high quality coatings at optimum coating rates.

The following examples illustrate various aspects of the present invention.

EXAMPLE 2

Composite particulates having compositions indicated as 2A, 2B and 2C in the Table below are prepared as follows. The indicated amounts of ingredients are mixed in dry powder form and added to the preheated spinning head of an Econofloss Model 3017 spinning machine, at a rotation speed of about 4000 rpm. The temperature is maintained at 150° C. for composition 2A, 130° C. for composition 2B and 115° C. for composition 2C. The resultant spun particulates are in the form of composite flakes having the compositions indicated in the Table below. Each of the particulate compositions dissolves completely within 3 minutes after adding to water, with only mild stirring in which no vortex is formed and no aeration occurs.

TABLE

|  | Wt. % |
|---|---|
| Composition 2A |  |
| Polydextrose | 50.0 |
| Hydroxypropyl cellulose | 5.0 |
| Hydroxylpropyl methylcellulose | 22.0 |
| Magnesium sterate | 5.0 |
| Titanium dioxide (fine grind) | 3.0 |
| FD&C yellow No. 6 aluminum lake (fine grind) | 5.0 |

TABLE-continued

|  | Wt. % |
|---|---|
| D&C yellow No. 10 aluminum lake fine grind) | 5.0 |
| Polyethylene glycol 3350 | 5.0 |
| Composition 2B |  |
| Corn syrup solids | 60.0 |
| Hydroxymethyl cellulose | 12.0 |
| Talc | 7.0 |
| FD&C blue #1 aluminum lake | 5.0 |
| D&C red #7 calcium lake | 2.0 |
| Triacetin | 7.0 |
| Sorbitol | 7.0 |
| Composition 2C |  |
| Sorbitol | 38.8 |
| Polydextrose | 25.0 |
| Hydroxypropyl cellulose | 12.0 |
| Hydroxymethyl cellulose | 12.0 |
| Propylene Glycol | 2.0 |
| Titanium dioxide | 5.0 |
| Talc | 5.0 |
| Colloidal silica | 0.2 |

EXAMPLE 3

The following powder ingredients are formed as a dry mixture: Corn syrup solids 30.0 weight %; Polydextrose 40.0 weight %; Hydroxypropyl cellulose 8.0 weight %; Hydroxypropyl methylcellulose 12.0 weight %; FD&C red No. 28 aluminum lake 5.0 weight %; and Polyethylene glycol 3350 5.0 weight %. This dry mixture is charged into the preheated head of a melt spinning device as in Example 2, and is spun at 150° C. to form particulate flakes. The particulate material is then dissolved in water by adding 400 grams of the particulate to 600 grams of deionized water in a stainless steel vessel while stirring with a conventional lab top mixer. A uniform dispersion is achieved in less than 3 minutes, thereby forming a tablet coating solution suitable for introduction into the pump reservoir of a conventional tablet coater.

EXAMPLE 4

A tablet coating solution is formed by adding 750 grams of particulate material having a composition as in Example 3 to 2,250 grams of purified water in a 5 liter stainless steel vessel while using a Tekmar lab top stirrer with a 5 cm, 4-prong blade. The coating solution is stirred for 1 minute. An 8.5 kg charge of uncoated tablets is placed in a 24 inch Accela-Cota tablet coater, manufactured by Thomas Engineering, Inc. The tablets are preheated until the bed temperature reaches 42° C. The pan rotation is then set to 12 rpm and the tablets are coated with the solution using a Binks Model 460 spray gun operating at 55 psi. The coating solution is pumped at a rate of between approximately 30–60 cc per minute using a peristalic pump. The tablet bed temperature is maintained between 42°–50° C. during the spray coating operation. After drying, the coating possesses a good appearance and favorable mechanical properties.

EXAMPLE 5

A coating solution is formed by adding 200 grams of particulates of composition 2A in Example 2 to 300 grams of deionized water in a 2 liter stainless steel vessel, while mixing using a spatula for 2 minutes. The resultant uniformly dispersed coating solution is added to the coating pan pump reservoir of a Vector LDCS tablet coater, manufactured by Vector Corp. A 1 kg charge of uncoated tablets is placed into the pan of the coater. The tablets are then preheated until the outlet air temperature of the coating pan reaches 4° C. The pan is then rotated at 20 rpm and the atomization air pressure is set to between 14–16 psi. The coating solution is sprayed at a rate of between approximately 5–8 cc per minute until the desired coating thickness is achieved. The coating possesses a good appearance and favorable mechanical properties.

It is understood that the above description of the present invention is susceptible to various modifications, changes and adaptations by those skilled in the art, and that such modifications, changes and adaptations are to be considered to be within the spirit and scope of the invention as set forth by the following claims.

What is claimed is:

1. A method for coating pharmaceutical tablets comprising the steps of:

(a) melt spinning a mixture comprising saccharide and polymer coating ingredients to form particulates;

(b) combining the particulates with water to form an aqueous solution, wherein the polymer coating ingredients of the particulates are rapidly dispersed in the water;

(c) contacting the tablets with the aqueous solution; and (d) drying the tablets.

2. The method according to claim 1, wherein the saccharide is selected from the group consisting of alcohol sugars.

3. The method according to claim 1, wherein the saccharide is selected from the group consisting of sucrose, lactose, maltose, polydextrose, dextrans, corn syrup, corn syrup solids, sorbitol, xylitol and combinations thereof.

4. The method according to claim 1, wherein the saccharide comprises from about 20 to about 99 weight % of the particulates.

5. The method according to claim 1, wherein the polymer of the coating ingredients is selected from the group consisting of hydroxypropyl methylcellulose, methylcellulose, hydroxypropyl cellulose, sodium alginate, povidone, gelatin and combinations thereof.

6. The method according to claim 1, wherein the polymer of the coating ingredients comprises hydroxypropyl methylcellulose.

7. The method according to claim 1, wherein the polymer coating ingredients comprise at least one plasticizer selected from the group consisting of triacetin, sorbitol, glycerin, polyethylene glycol and propylene glycol.

8. The method according to claim 1, wherein the polymer coating ingredients comprise at least one colorant selected from the group consisting of dyes, lakes and natural colorants.

9. The method according to claim 1, wherein the polymer coating ingredients comprise at least one metal oxide opacifier.

10. The method according to claim 1, wherein the particulates have an average size of from about 0.1 to about 8 millimeters.

11. The method according to claim 1, wherein the particulates have an aspect ratio of less than about 20:1.

12. The method according to claim 1, wherein the particulates are in the form of flakes.

13. The method according to claim 1, wherein the particulates are combined with water by adding the particulates to water and mixing.

14. The method according to claim 13, wherein the polymer coating ingredients of the particulates are substantially uniformly dissolved in the water in less than about 3 minutes.

15. The method according to claim 13, wherein the mixing is performed at a low shear rate.

16. The method according to claim 1, wherein the tablets are contacted with the aqueous mixture by spray coating.

17. The method according to claim 1, wherein the tablets are dried by forced air.

* * * * *